US008473031B2

(12) United States Patent
Nixon et al.

(10) Patent No.: US 8,473,031 B2
(45) Date of Patent: Jun. 25, 2013

(54) MEDICAL ROBOTIC SYSTEM WITH FUNCTIONALITY TO DETERMINE AND DISPLAY A DISTANCE INDICATED BY MOVEMENT OF A TOOL ROBOTICALLY MANIPULATED BY AN OPERATOR

(75) Inventors: Thomas R. Nixon, Santa Clara, CA (US); Margaret M. Nixon, Santa Clara, CA (US); William C. Nowlin, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1333 days.

(21) Appl. No.: 11/964,215

(22) Filed: Dec. 26, 2007

(65) Prior Publication Data

US 2009/0171371 A1    Jul. 2, 2009

(51) Int. Cl.
  *A61B 5/05* (2006.01)
(52) U.S. Cl.
  USPC ....................................... 600/424
(58) Field of Classification Search
  USPC ..... 600/407, 476; 901/41, 46, 47, 6; 345/629, 345/634
  See application file for complete search history.

(56) References Cited

U.S. PATENT DOCUMENTS

| | | | |
|---|---|---|---|
| 4,312,363 A | | 1/1982 | Rothfuss et al. |
| 4,922,909 A | * | 5/1990 | Little et al. ............ 600/300 |
| 6,498,944 B1 | | 12/2002 | Ben-Haim et al. |
| 6,594,552 B1 | | 7/2003 | Nowlin et al. |
| 7,166,112 B2 | | 1/2007 | Hawkins et al. |
| 7,182,770 B2 | | 2/2007 | Falahee |
| 2003/0109780 A1 | | 6/2003 | Coste-Maniere et al. |
| 2004/0243147 A1 | | 12/2004 | Lipow |
| 2005/0193451 A1 | * | 9/2005 | Quistgaard et al. ............ 901/9 |
| 2006/0041181 A1 | | 2/2006 | Viswanathan et al. |
| 2006/0161045 A1 | | 7/2006 | Merril et al. |

FOREIGN PATENT DOCUMENTS

| | | |
|---|---|---|
| EP | 469966 A1 | 2/1992 |
| EP | 1125557 A2 | 8/2001 |
| FR | 2660185 A1 | 10/1991 |

OTHER PUBLICATIONS

PCT/US08/86249 International Search Report, mailed Mar. 27, 2009, 4 pages.
PCT/US08/86249 Written Opinion of the International Search Authority, mailed Mar. 27, 2009, 7 pages.
Vertut, Jean and Philippe Coiffet, *Teleoperation and Robotics: Evolution and Development*, English translation Prentice-Hall, Inc., Inglewood Cliffs, NJ, USA, 1986.
Kim Miriam et al., "Computer Assisted 3D Measurements for Micro-Surgery," Proceedings of the Human Factors and Ergonomics Society 41st Annual Meeting, 1997, pp. 787-791, Human Factors and Ergonomics Society.

* cited by examiner

*Primary Examiner* — Parikha Mehta

(57) ABSTRACT

A medical robotic system has functionality to determine and display information of a distance indicated by movement of one or more tools being robotically manipulated by an operator. The distance is determined using sensed robotic manipulation of the one or more tools. Information of the distance is displayed on the monitor so as to be visually associated with the movement and/or positions of the tools, such as a virtual tape measure that extends along with or between images of the one or more tools on the monitor or as a virtual ruler with the distance being indicated by a pointer. Alternatively, information of the distance may simply be indicated on a digital read-out shown on the monitor that is displayed and continually updated with the movement of the one or more tools.

31 Claims, 11 Drawing Sheets

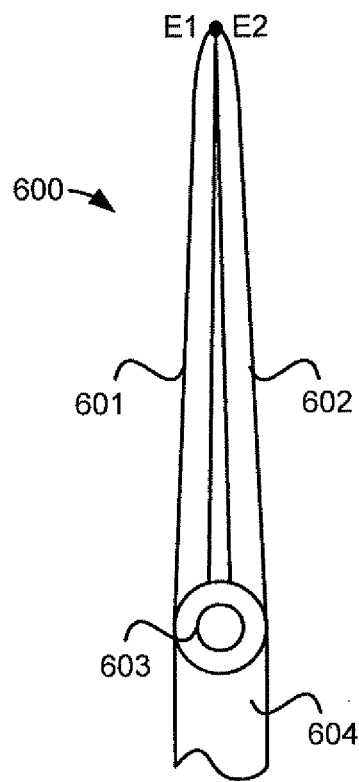
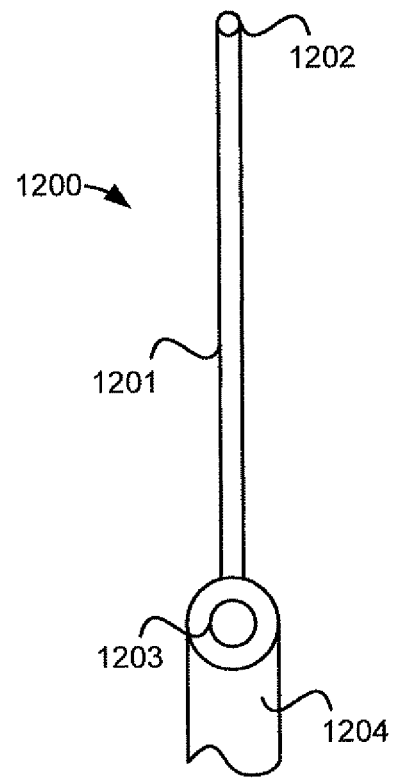
fig.14
fig.13
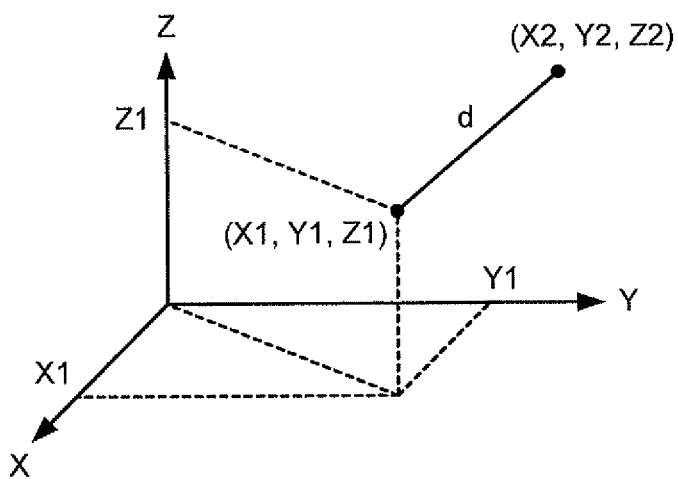
fig.12

MEDICAL ROBOTIC SYSTEM WITH FUNCTIONALITY TO DETERMINE AND DISPLAY A DISTANCE INDICATED BY MOVEMENT OF A TOOL ROBOTICALLY MANIPULATED BY AN OPERATOR

FIELD OF THE INVENTION

The present invention generally relates to medical robotic systems and in particular, to a medical robotic system with functionality to determine and display a distance indicated by movement of a tool robotically manipulated by an operator.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist so that when added to the motions of manipulators holding the surgical instruments, they allow at least six degrees of freedom of motion, which is comparable to or even greater than the natural motions of open surgery.

The da Vinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more robotic arm assemblies with corresponding slave manipulators for holding and manipulating medical devices such as surgical instruments (or other tools) and image capturing devices for performing and/or viewing a medical procedure at a surgical site within a patient. To manipulate these medical devices, the surgeon's console also includes input devices which may be selectively associated with the medical devices and their respective slave manipulators. Since the movements of the input devices and their associated medical devices are scaled, this allows the surgeon to perform intricate medical procedures with greater ease than conventional open surgery as an operator of the medical robotic system. Further, it may even allow the surgeon to perform medical procedures that are not even feasible using conventional open surgery techniques.

To perform a minimally invasive surgical procedure on a patient, one or more incisions are first made in the patient and cannulae inserted therein to gain access to a surgical site within the patient. Setup arms supporting the slave manipulators are then positioned so as to allow the slave manipulators to attach to respective of the cannulae. Surgical instruments engaged on the slave manipulators are then inserted into the cannulae and properly positioned and oriented in order to perform the procedure. A surgeon may then manipulate input devices which are coupled to the slave manipulators and their respective surgical instruments through one or more controllers to perform the surgical procedure.

During the performance of a medical procedure it may be advantageous to measure the size of an object or a distance between objects in vivo. For example, the surgeon may desire to measure the size of an abnormal growth or diseased tissue before its removal or treatment, measure the size of a hole in a tissue or other anatomic structure to gauge the extent of its deterioration, or measure the size of a gap between tissue or other anatomic structures to determine whether surgical instruments or other medical devices may be able to pass through it to a surgical site.

OBJECTS AND SUMMARY OF THE INVENTION

Accordingly, one object of one or more aspects of the present invention is a method for determining and displaying information of an operator indicated distance using a medical robotic system.

Another object of one or more aspects of the present invention is a medical robotic system with functionality to determine and display a distance indicated by movement of a tool robotically manipulated by an operator.

These and additional objects are accomplished by the various aspects of the present invention, wherein briefly stated, one aspect is a method for determining and displaying information of an operator indicated distance using a medical robotic system, comprising: capturing images indicating movement of a tool as the tool is being robotically manipulated by an operator using the medical robotic system; sensing the robotic manipulation of the tool; determining a distance moved by the tool using the sensed robotic manipulation of the tool; and displaying the captured images and information of the distance on a monitor of the medical robotic system so as to indicate movement of the tool and visually associate the information of the distance with the movement of the tool.

Another aspect is a medical robotic system comprising: a tool, a robotic arm, an image capturing device, a monitor, an input device, and a processor. The robotic arm is adapted to move the tool and has at least one sensor to sense movement of the tool. The image capturing device is positioned to capture an image of the tool. The processor is configured to move the robotic arm and the tool in response to operator manipulation of the input device, display images received from the image capturing device on the monitor, determine a distance moved by the tool using data received from the at least one sensor, and display information of the determined distance on the monitor so as to indicate movement of the tool and visually associate the information of the distance with the movement of the tool.

Another aspect is a method for determining and displaying information of an operator indicated distance using a medical robotic system, comprising: sensing positions of first and second tools being robotically manipulated by the operator so as to indicate a distance to be measured using the first and second tools; determining the distance between the first and second tools using the sensed positions of the first and second tools; and displaying information of the distance on a monitor of the medical robotic system.

Still another aspect is a medical robotic system comprising: first and second tools, first and second robotic arms, a monitor, first and second input devices, and a processor. The first robotic arm is adapted to move the first tool and has at least one first sensor to sense movement of the first tool. The a second robotic arm is adapted to move the second tool and has at least one second sensor to sense movement of the second tool. The processor is configured to move the first robotic arm and the first tool in response to operator manipulation of the first input device, move the second robotic arm and the second tool in response to operator manipulation of the second input device, determine a distance between the first and second tools using data received from the at least one first sensor and the at least one second sensor, and display information of the determined distance on the monitor.

Additional objects, features and advantages of the various aspects of the present invention will become apparent from the following description of its preferred embodiment, which description should be taken in conjunction with the accompanying drawings.

BRIEF DESCRIPTION OF THE DRAWINGS

FIG. 12 illustrates a three-dimensional coordinate system with two representative points and an indicated distance between the points.

FIG. 13 illustrates a tool having a force sensitive tip with small contact area for use in a medical robotic system utilizing aspects of the present invention to measure larger operator robotically specified distances.

FIG. 14 illustrates a tool having first and second pivotally coupled elements in a closed position for use in a medical robotic system utilizing aspects of the present invention to measure larger operator robotically specified distances.

DETAILED DESCRIPTION OF THE PREFERRED EMBODIMENT

Figure 1:
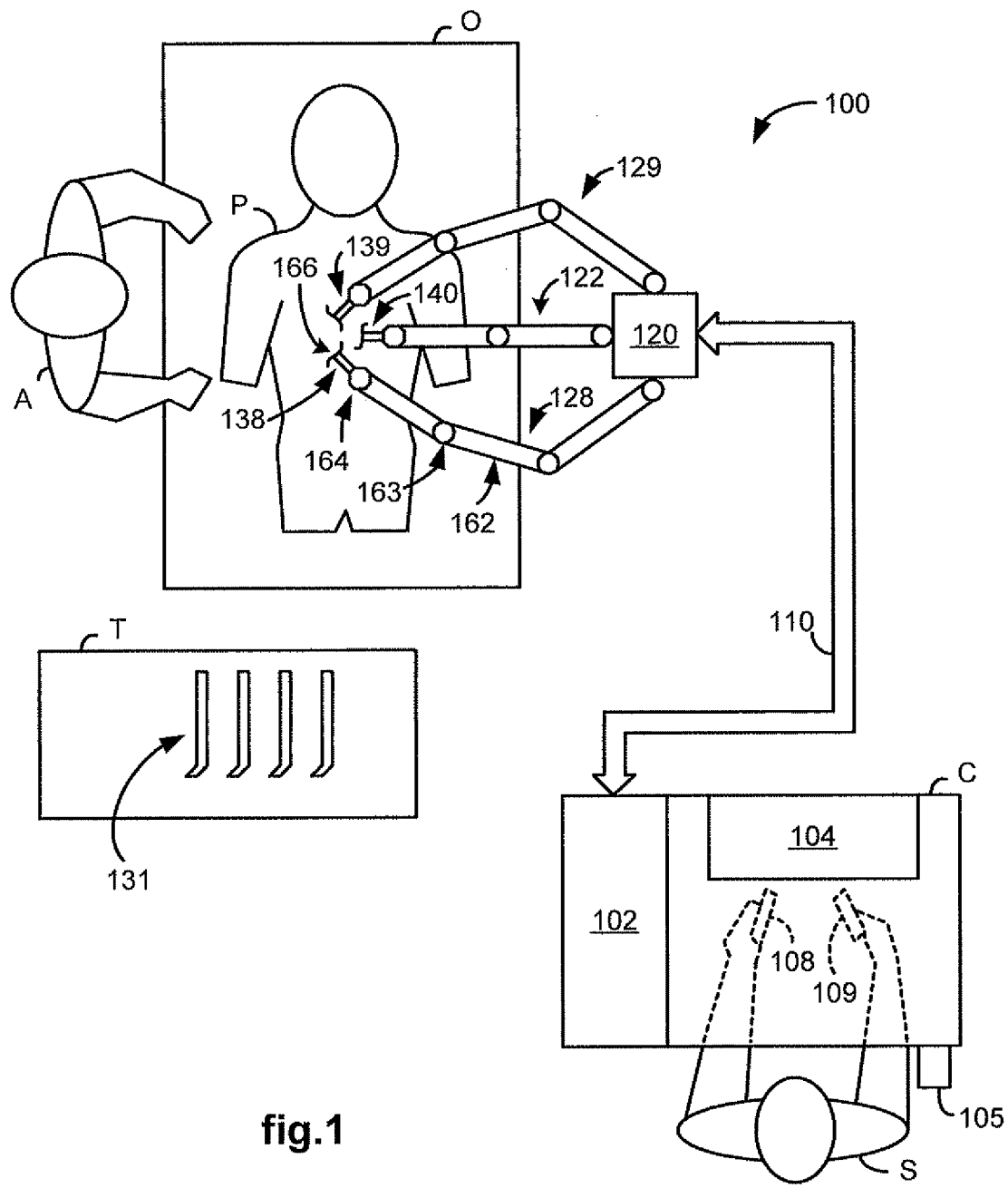
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is reclining on an Operating table ("O").

The Console includes a 3-D monitor 104 for displaying a 3-D image of a surgical site to the Surgeon, left and right manipulatable input devices 108, 109, a foot pedal 105, and a processor 102. The input devices 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the system 100.

The Surgeon performs a medical procedure by manipulating the input devices 108, 109 (also referred to herein as "master manipulators") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by a stereoscopic endoscope 140.

Each of the tools 138, 139, as well as the Endoscope 140, is conventionally inserted through a tool guide (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room.

Each of the robotic arm assemblies 122, 128, 129 includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of input devices 108, 109 to their respective slave manipulators of robotic arm assemblies 128, 129 by generating and transmitting digital control signals over bus 110 so that the Surgeon can effectively manipulate their respective tools 138, 139. Another important function is to implement various sub-processors such as those shown and described in reference to FIGS. 3, 4 and the method shown and described in reference to FIG. 19.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware, and distributed, in a distributed processing fashion, about the system 100.

For additional details on the construction and operation of medical robotic systems such as described herein, see, e.g., commonly owned U.S. Pat. No. 6,493,608 "Aspects of a Control System of a Minimally Invasive Surgical Apparatus," and commonly owned U.S. Pat. No. 6,424,885 "Camera Referenced Control in a Minimally Invasive Surgical Apparatus," which are incorporated herein by reference.

Figure 2:
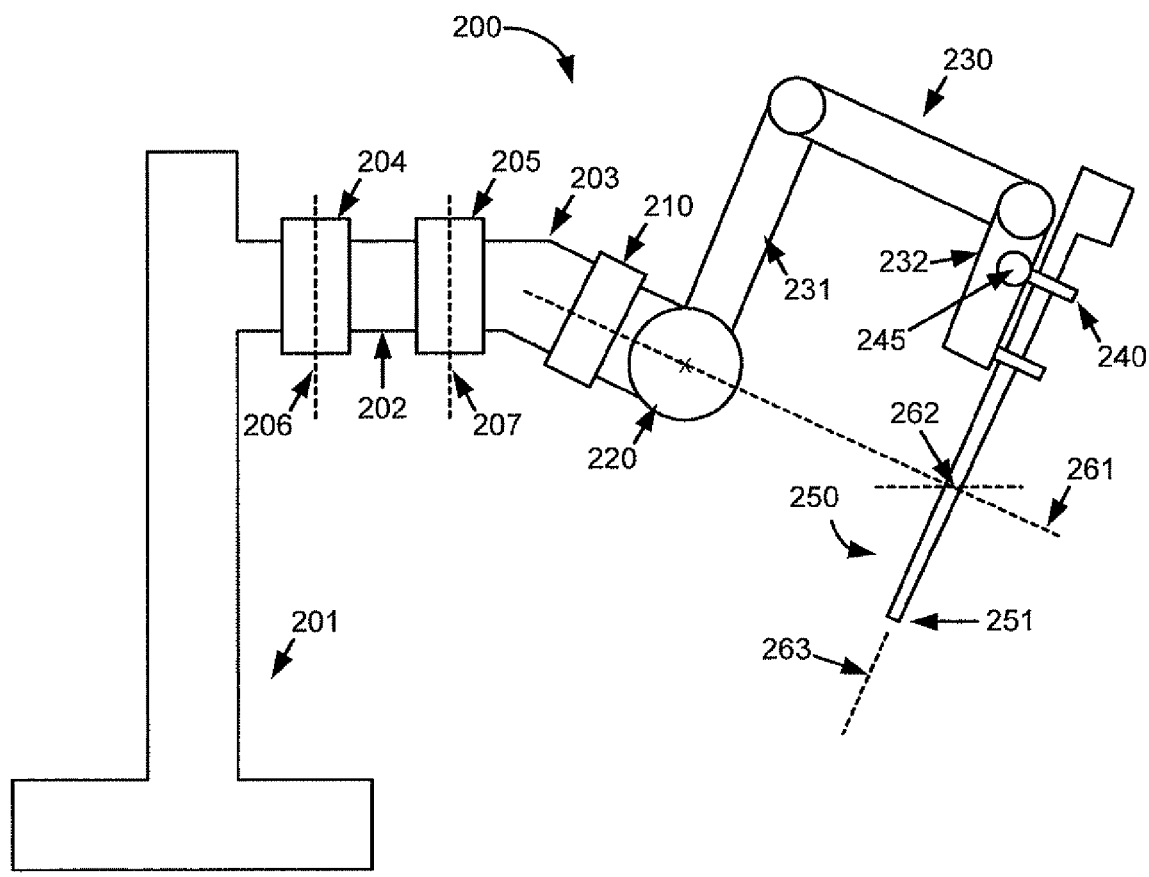
FIG. 2 illustrates a side view of a simplified robotic arm assembly of a medical robotic system utilizing aspects of the present invention.

FIG. 2 illustrates, as an example, a side view of a simplified (not necessarily in proportion or complete) robotic arm assembly 200 (which is representative of the robotic arm assemblies 128, 129) holding a tool 250 (such as tools 138, 139 and other tools described herein) for performing a medical procedure. The tool 250 is removably held in tool holder 240. The robotic arm assembly 200 is mechanically supported by a base 201, which may be part of a patient-side movable cart or affixed to the operating table or ceiling. It includes links 202, 203 which are coupled together and to the base 201 through horizontal setup joints 204, 205.

The setup joints 204, 205 in this example are passive joints that allow manual positioning of the arm 200 when their brakes are released. For example, setup joint 204 allows link 202 to be manually rotated about axis 206, and setup joint 205 allows link 203 to be manually rotated about axis 207. The setup arm or portion of the robotic arm assembly 200 includes these setup joints.

Although only two links and two setup joints are shown in this example, more or less of each may be used as appropriate in this and other robotic arm assemblies in conjunction with the present invention. For example, although setup joints 204, 205 are useful for horizontal positioning of the arm 200, additional setup joints may be included and useful for limited vertical and angular positioning of the arm 200. For major vertical positioning of the arm 200, however, the arm 200 may also be slidably moved along the vertical axis of the base 201 and locked in position.

The robotic arm assembly 200 also includes three active joints driven by motors (or more generally, actuators). A yaw joint 210 allows arm section 230 to rotate around an axis 261, and a pitch joint 220 allows arm section 230 to rotate about an axis perpendicular to that of axis 261 and orthogonal to the plane of the drawing. The slave manipulator of the robotic arm assembly 200 includes these active joints.

The arm section 230 is configured so that sections 231, 232 are always parallel to each other as the pitch joint 220 is rotated by its motor. As a consequence, the tool 250 may be controllably moved by driving the yaw and pitch motors so as to pivot about the pivot point 262, which is generally located through manual positioning of the setup joints 204, 205 so as to be at the point of incision into the patient. In addition, an insertion gear 245 may be coupled to a linear drive mechanism (not shown) to extend or retract the tool 250 along its axis 263.

Although each of the yaw, pitch, and insertion joints or gears, 210, 220, 245, is controlled by an individual joint or gear controller, the three controllers are controlled by a common master/slave control system so that the slave manipulator of the robotic arm assembly 200 may be controlled through user (e.g., surgeon) manipulation of its associated master manipulator.

Figure 3:
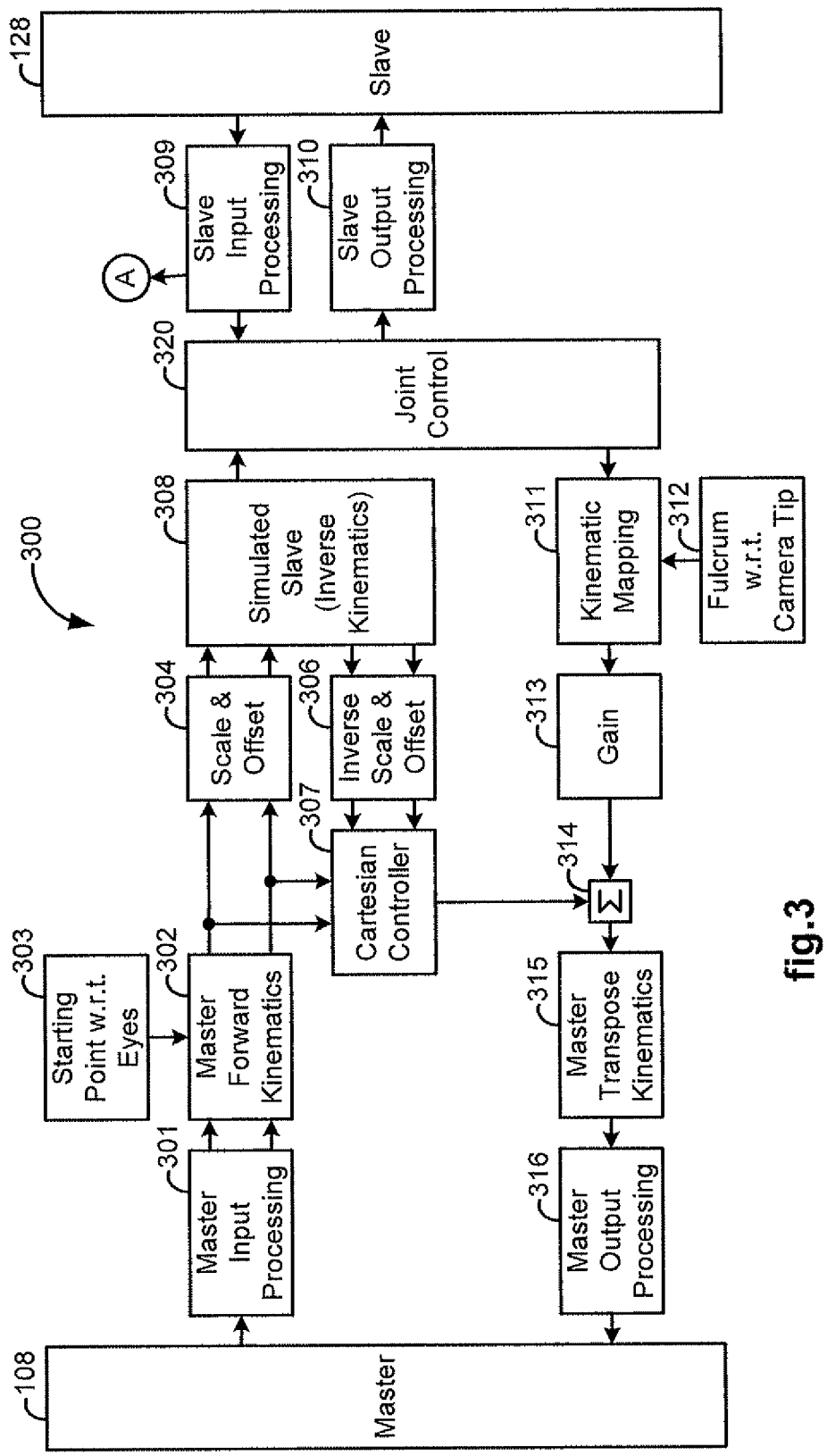
FIG. 3 illustrates a block diagram of a master/slave control system of a medical robotic system utilizing aspects of the present invention.

FIG. 3 illustrates, as an example, a block diagram of a master/slave control system 300 for controlling movement of the slave manipulator of the robotic arm assembly 128 and consequently, the position and orientation of its attached tool 138, as commanded by movement of the master manipulator 108 by a surgeon. A similar control system may also be provided for the slave manipulator of the robotic arm assembly 129 and its associated master manipulator 109. All control systems described herein may be implemented as digital control systems in the processor 102.

Both the master and slave manipulators include a number of linkages connected by joints so as to facilitate multiple degrees-of-freedom movement. As the surgeon moves the master manipulator 108 from one position to another during the course of performing a surgical procedure, sensors associated with the master manipulator joints provide information indicating such command movement in master joint space, and sensors associated with the slave manipulator joints provide information indicating slave manipulator and consequently, tool 138 movement in slave joint space for feedback purposes. In order to better detect and control fine movements of their respective joints, high resolution encoders are preferably used for the joint sensors.

A master input processor 301 receives the information of the master joint positions, which are sampled at the control system processing rate, from the master joint sensors in the master manipulator 108 and computes joint velocities from the sensed joint positions. A master forward kinematics processor 302 receives the master joint positions and velocities from the master input processor 301 and transforms them from master joint space to corresponding positions and velocities of the master frame (i.e., the frame associated with the master manipulator 108) in Cartesian space relative to the eye reference frame (i.e., the reference frame associated with the position of the surgeon's eyes), using, for example, a Jacobian matrix and eye related information separately determined and provided in block 303.

A scale and offset processor 304 receives the Cartesian position and velocity commands from the master forward kinematics processor 302, scales the commanded movement according to a scale factor selected to perform the surgical procedure, and takes into account offsets to generate desired slave tool frame (i.e., the frame associated with the tool 138) positions and velocities. The scale adjustment is useful where small movements of the slave manipulator of the robotic arm assembly 128 are desired relative to larger movement of the master manipulator 108 in order to allow more precise movement of the slave tool 138 at the surgical site. The offsets, on the other hand, determine, for example, the corresponding position and/or orientation of an end effector frame (i.e., the frame associated with an end effector of the tool 138) in the camera reference frame (i.e., the frame associated with the distal tip of the endoscope 140) relative to a position and orientation of the master frame in the eye reference frame.

A simulated slave processor 308 receives desired slave tool frame position and velocity commands from the scale and offset processor 304 and limits the desired slave tool frame position, orientation, and velocities to assigned Cartesian Limits, for instance to enforce correct and intuitive operation of the tool 138 by keeping it within its dexterous workspace. The simulated slave processor 308 generates simulated slave joint positions and velocities corresponding to the limited slave tool frame positions and velocities while making sure that the generated slave joint positions and velocities do not exceed the actual slave joint's range of motion and maximum velocities (i.e., joint limits) even in the vicinity of kinematic singularities for the slave kinematics.

An inverse scale and offset processor 306 receives the simulated joint position and velocity commands from the simulated slave processor 308 and performs an inverse function to that of the scale and offset processor 304 on these commands. A Cartesian controller 307 receives as first inputs, the inputs to the scale and offset processor 304 and as second inputs, the outputs of the inverse scale and offset processor 306. The Cartesian controller 307 then generates an error signal as a difference of the first and second inputs and a Cartesian force "$F_{CART}$" from the error signal such as with the following formula:

$$F_{CART}=K(\Delta x)+B(\Delta \dot{x}) \qquad (1)$$

where "K" is a spring constant, "B" is a damping constant, "$\Delta \dot{x}$" is the difference between the Cartesian velocity inputs to the Cartesian controller 307 and "$\Delta x$" is the difference between the Cartesian position inputs to the Cartesian controller 307. For an orientation error, a corresponding torque in Cartesian space is determined.

A master transpose kinematics processor 315 receives the Cartesian force $F_{CART}$ through a summation node 314, and generates a corresponding torque in joint space using, for example, the Jacobian transpose matrix and kinematic relationships associated with the master manipulator 108. A master output processor 316 receives the master torque signals from the master transpose kinematics processor 315, generates electrical currents corresponding to the master torque signals, and supplies the electrical currents to corresponding master joint motors of the master manipulator 108. As a result, a surgeon operating the master manipulator 108 feels the Cartesian force $F_{CART}$ whenever the surgeon is commanding a position or velocity which exceeds system Cartesian or slave joint limits or would result in a kinematic singularity condition for the slave manipulator of the robotic arm assembly 128.

As the master input processor 301 is receiving master joint positions from sensors in the master manipulator 108, a slave input processor 309 is also receiving slave joint positions from position sensors in the slave manipulator at the control system processing rate. A joint control unit 320 receives the slave joint positions from the slave input processor 309 and the simulated joint position commands provided from the simulated slave processor 308 and generates slave torque command signals for the slave joint motors and master torque feedback command signals for the master joint motors.

The slave torque command signals are generated by the joint control unit 320 so as to drive joints of the slave manipulator until feedback errors calculated in the joint control unit 320 zero out. A slave output processor 310 receives the slave torque command signals from the joint control unit 320, converts them into appropriate electrical currents, and supplies the electrical currents to the joint motors of the slave manipulator so as to drive the motors accordingly.

The master torque feedback command signals are generated by the joint control unit 320 as a function of the slave joint position and velocity tracking errors so as to reflect forces being exerted against the tool 138 or its slave manipulator back to the master manipulator 108 so that these forces may be felt by the surgeon. A kinematic mapping unit 311 receives the master torque feedback command signals from the joint control unit 320 and generates the corresponding Cartesian force at the tip of the tool 138 relative to the camera frame of the endoscope 140 using the slave kinematic configuration and the previously calculated slave fulcrum (e.g., pivot point) position information provided in block 312.

A gain 313 adjusts the magnitude of the Cartesian force so as to ensure system stability while providing adequate force sensation to the surgeon. The gain-adjusted Cartesian force is then passed through the summation node 314 and processed along with the Cartesian force provided by the Cartesian controller 307 through the Master transpose kinematics processor 315 and Master output processor 316 as previously described in reference to their processing of the Cartesian force provided by the Cartesian controller 307.

Additional details related to conventional aspects of the master/slave control system 300, such as the various reference frames referred to herein and the calculation of the surgeon eye related information provided in block 303 and the slave fulcrum information provided in block 312, which are based upon well-known mathematics, are described, for example, in previously incorporated by reference and commonly owned U.S. Pat. No. 6,424,885, "Camera Referenced Control in a Minimally Invasive Surgical Apparatus."

The joint control unit 320 includes a joint controller for each active joint and gear of the slave manipulator of the robotic arm assembly 128 that is being controlled by the master/slave control system 300. In particular, where the slave manipulator 128 includes a yaw joint 210, a pitch joint 220, and an insertion axis gear 245 such as the robotic arm assembly 200 of FIG. 2, each of these joints or gears will have its own controller. To simplify the description herein and in the claims, the term "joint" is to be understood as a connection (translational or revolute) between two links and may include gears as well as any other controllable component coupled to drive mechanisms that may be used in controlling robotic arm assemblies.

Figure 4:
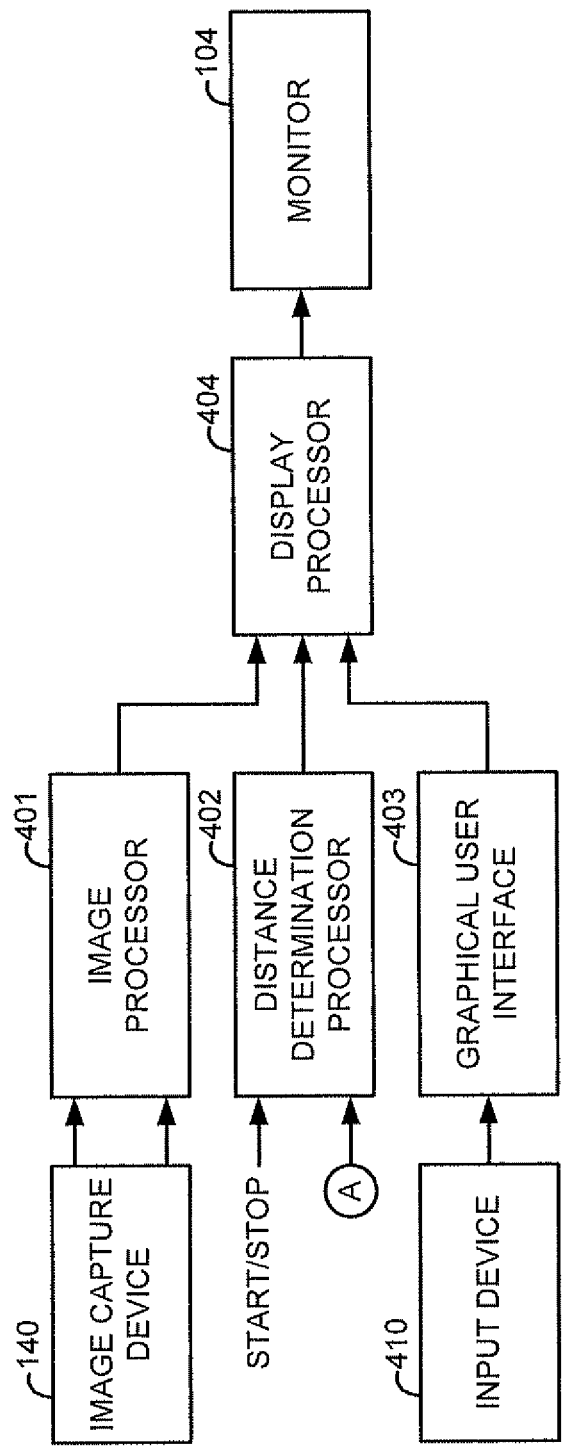
FIG. 4 illustrates a block diagram of monitor related processors and a graphical user interface used in a medical robotic system utilizing aspects of the present invention.

FIG. 4 illustrates, as an example, a block diagram including various processors and a graphical user interface implemented in or using the processor 102 that process information received from the image capturing device 140, the slave input processor 309 of the master/slave control system 300, and an operator manipulated input device 410 to perform a method for determining and displaying information of an operator indicated distance on the monitor 104 of the medical robotic system 100. Images captured by the image capture device 140 are processed in a conventional manner by an image processor 401 and a display processor 404 so as to be displayed (in their processed form) three-dimensionally on the monitor 104.

A distance determination processor 402 processes slave joint positions, which are sensed by encoders in the slave manipulator of the robotic arm assembly 128 and received from the slave input processor 309 of the master/slave control system 300, to determine distances moved by their manipulated tool. To determine the distances that the tool moves, the slave joint positions are processed using forward kinematics of the slave manipulator in a similar fashion as the master joint positions are processed by the master input processor 301 and forward kinematics processor 302. In this case, however, the slave joint positions are transformed from slave joint space to corresponding positions and velocities of the tool frame in Cartesian space relative to a fixed reference frame which may be defined at a fixed position in the operating room such as the base of the patient-side cart 120. Start and stop indications may be provided to the distance determination processor 402 so that distance determinations start after receiving the start indication and stop after receiving the stop indication.

A graphical user interface 403 displays an interactive menu on the monitor 104 (or other computer display screen) which the operator may interact with using an input device 410 (such as a conventional computer mouse) to specify various display options for the display processor 404, such as the type and manner in which the distance information is to be displayed on the monitor 104. The graphical user interface 403 may also display clickable icons on the monitor 104 which the operator may click on using the input device 410 to generate the start and stop indications provided to the distance determination processor 402.

The display processor 404 receives the distance information from the distance determination processor 402 and the display options from the graphical user interface 403 and displays the distance information on the monitor 104 according to the specified display options along with the processed image information received from the captured image processor 401. Examples of such display processing and the various distance measurement and display options provided through the graphical user interface 403 are further described below.

Figure 5:
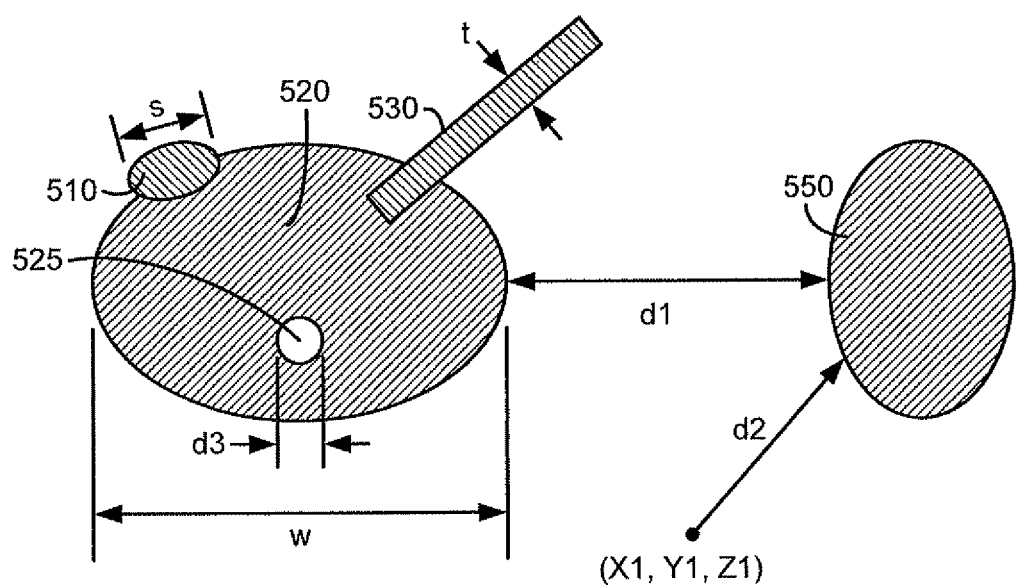
FIG. 5 illustrates representative measurements that may be determined by a medical robotic system utilizing aspects of the present invention.

FIG. 5 illustrates, as examples, representative measurements that may be determined by the medical robotic system 100. As one example, the width "w" of an anatomic structure 520 may be measured. As another example, a size "s" of a growth 510 on an anatomic structure may be measured. As another example, a diameter "d3" of a hole or opening 525 in the anatomic structure 520 may be measured. As another example, a thickness "t" of a vessel 530 may be measured. As another example, a distance "d1" between two anatomic structures 520, 550 may be measured. As still another example, a distance "d2" from a specified point (X1, Y1, Z1) to the anatomic structure 550 may be measured.

Figure 6:
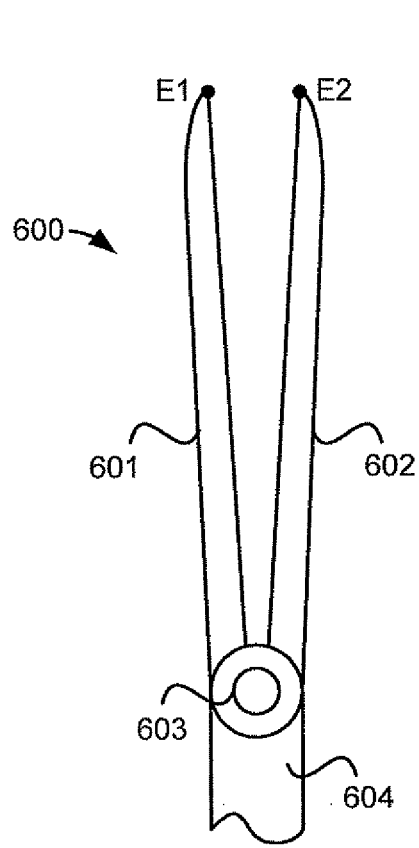
FIG. 6 illustrates a tool having first and second pivotally coupled elements that may be used as a measuring device in a medical robotic system utilizing aspects of the present invention.

FIG. 6 illustrates, as an example, a tool 600 having first 601 and second 602 elements which are coupled at and pivot about a joint 603 coupled to a shaft 604 so as to be capable of measuring inner and outer diameters associated with anatomic structures by its opened position. For example, the tool 600 may be used to measure an outer diameter of an object, such as the thickness "t" of the vessel 530 or size "s" of the growth 510 between tips E1 and E2 of its first 601 and second 602 elements. Also, as the tool 600 may be used to measure an inner diameter of an opening such as the diameter "d3" of the opening 525 in the anatomic structure 520 between the tips E1 and E2 of its first 601 and second 602 elements. The tool 600 may be any one of a number of standard surgical tools such as forceps or scissors that are manipulated by a slave manipulator of a robotic arm assembly in a similar manner that the tools 138, 139 are manipulated by slave manipulators of the robotic arm assemblies 128, 129. The open positions of the tool 600 are calibrated so that accurate measurements of the type described herein may be made.

Although the tips E1, E2 of the first and second elements 601, 602 are described as being used herein for performing measurements with the tool 600, other marked and calibrated points on the first and second elements 601, 602 may also be used. For example, calibrated reference points on the inner sides of the first and second elements 601, 602 may be used for measuring items such as the growth 510 or the vessel 530. Also, calibrated reference points on the outer sides of the first and second elements 601, 602 may be used for measuring items such as the opening 525.

Figure 7:
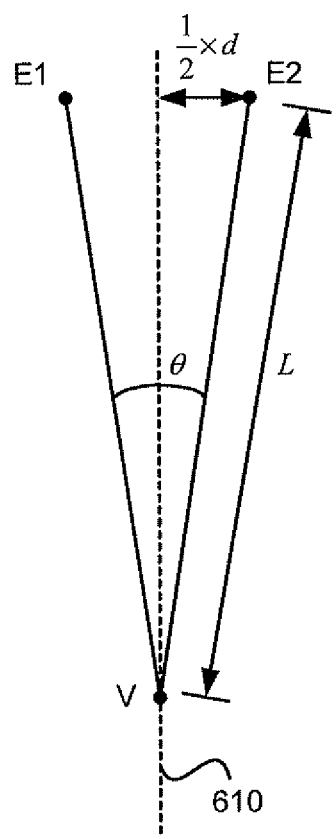
FIG. 7 illustrates geometry used in calculating a distance measured by the tool of FIG. 6 utilizing aspects of the present invention.

FIG. 7 illustrates, as an example, geometry used in calculating a distance "d" measured by the tool 600. By application of the geometry, the distance "d" is readily calculated from the opening angle "θ" of the tool 600 using the following equation:

$$d = 2 \times L \times \sin\left(\frac{\theta}{2}\right) \quad (2)$$

where "L" is the length of each of the first and second elements 601, 602 from its tip (E1 or E2) to a center "V" of the tool's joint 603. In this example, the longitudinal axis 610 of the shaft 604 is assumed to bisect the opening angle "θ" and the distance to be determined (i.e., measured) is between the tips E1, E2.

Figure 8:
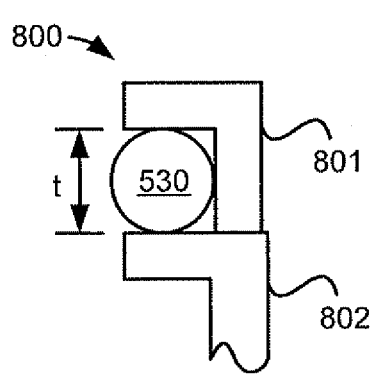
FIGS. 8-9 illustrate a tool having first and second linearly displaceable elements that may be used as a measuring device in a medical robotic system utilizing aspects of the present invention.
Figure 9:
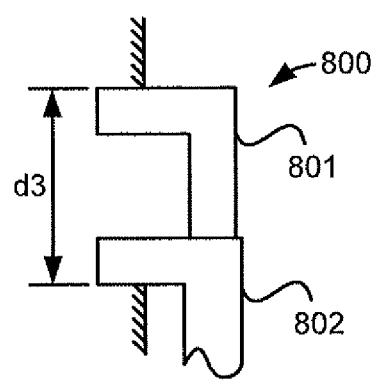

FIGS. 8-9 illustrate, as another example, a tool 800 having first 801 and second 802 linearly displaceable elements that may be used as a caliper to measure inner and outer diameters associated with anatomic structures. For example, as shown in FIG. 8, the tool 800 may be used to measure an outer diameter of an object, such as the thickness "t" of the vessel 530 or size "s" of the growth 510, between inner surfaces of its first 801 and second 802 elements. Further, as shown in FIG. 9, the tool 800 may be used to measure an inner diameter of an opening such as the diameter "d3" of the opening 525 in the anatomic structure 520 using the outer surfaces of its first 801 and second 802 elements. The tool 800 is a specialized tool whose open positions are preferably calibrated so that accurate measurements of the type described herein may be made. Like the tools 138, 139, 600, the tool 800 is also manipulated by and operated through a slave manipulator of a robotic arm assembly.

As may be readily appreciated, measuring distances by the open position of the tools 600, 800, as described above, is limited by their maximum open positions. For measuring larger distances, a different approach is described below.

Figure 10:
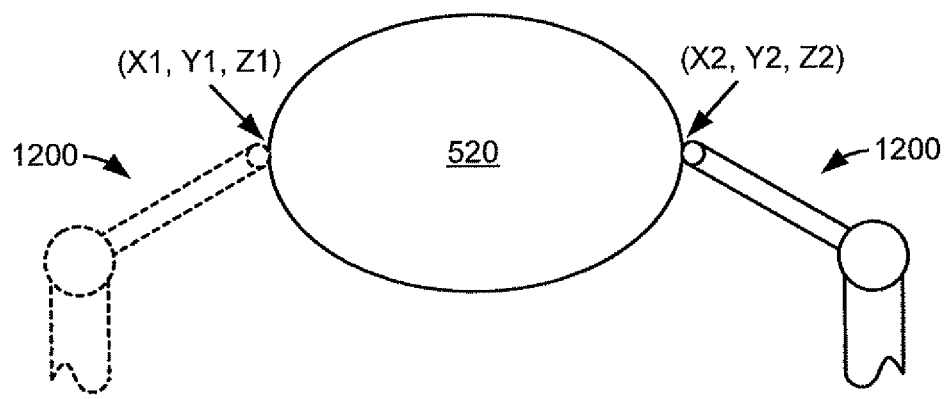
FIG. 10 illustrates a single tool, measurement technique for measuring larger operator robotically specified distances using a medical robotic system utilizing aspects of the present invention.
Figure 11:
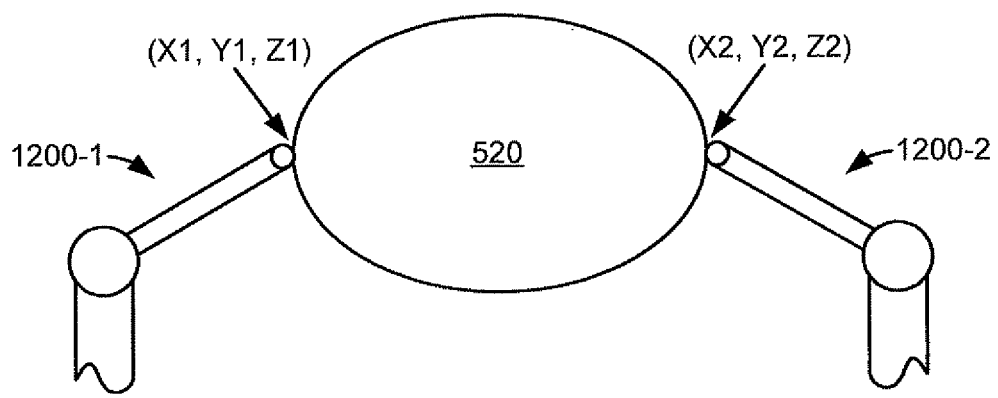
FIG. 11 illustrates a two tool, measurement technique for measuring larger operator robotically specified distances using a medical robotic system utilizing aspects of the present invention.

FIGS. 10 and 11 illustrate, as examples, a measurement technique for measuring larger distances than those measurable by opening the tools 600, 800 as described above. In these examples, a width "w" of the anatomic structure 520 is measured by indicating two points (X1, Y1, Z1), (X2, Y2, Z2) on opposing sides of the anatomic structure 520 using a tip of one robotically manipulated tool 1200 as shown in FIG. 10 or the tips of two robotically manipulated tools 1200-1, 1200-2 as shown in FIG. 11 so that the distance determination processor 402 can compute a distance between the two points.

For example, FIG. 12 illustrates a three-dimensional coordinate system in the fixed reference frame with the two points (X1, Y1, Z1), (X2, Y2, Z2) and a distance "d" indicated between the two points which may be calculated in a conventional manner as:

$$d = \sqrt{(X1-X2)^2 + (Y1-Y2)^2 + (Z1-Z2)^2} \quad (3)$$

FIG. 13 illustrates, as an example, a tool 1200 which may be used to indicate the two points (X1, Y1, Z1), (X2, Y2, Z2) on the surface of the anatomic structure 520. The tool 1200 has a slender element 1201 with a force sensor 1202 on its tip. The tip has a contact surface area of proper size to provide accurate position indications without damaging tissue that it may come into contact with. A wrist mechanism 1203 allows the slender element 1201 to be robotically manipulated to different orientations. A shaft 1204 is coupled to an interface (not shown) which in turn, is coupled to a robotic arm assembly in the same manner as the tools 138, 139 are coupled to and robotically manipulated by slave manipulators of their respective robotic arm assemblies 128, 139.

Referring back to FIG. 10, the tool 1200 is shown in two positions. In a first position, the tool 1200 is shown in dotted outline form to indicate a prior position of the tool 1200 as its tip sensor 1202 is touching a left side of the anatomic structure 520 at the point (X1, Y1, Z1). In a second position, the tool 1200 is shown in solid outline form to indicate a current position of the tool 1200 as its tip sensor 1202 is touching a right side of the anatomic structure 520 at the point (X2, Y2, Z2). When the force sensor 1202 makes contact with the anatomic structure 520 at the points (X1, Y1, Z1), (X2, Y2, Z2), such contact generates start and stop indications for the distance determination processor 402 so that the final distance determined by the unit 402 (e.g., after receiving the stop indication) is the width "w" of the anatomic structure 520.

On the other hand, when two tools 1200-1, 1200-2 are used (as shown in FIG. 11), instead of the single tool 1200 (as shown in FIG. 10), to indicate the points (X1, Y1, Z1), (X2, Y2, Z2) on the anatomic structure 520, a single measurement command may be provided by the operator (as opposed to the start and stop indications used with the single tool 1200) to indicate the points (X1, Y1, Z1), (X2, Y2, Z2) that are to be used by the distance determination processor 402 for its distance calculation. In either case (i.e., using a single tool or two tools to indicate the beginning and end points for the distance calculation), the distance calculation performed by the distance determination processor 402 is the same. Prior to making a measurement using the two tools 1200-1, 1200-2, the operator may first touch their tip/sensors together in order to define an absolute zero point for displacement/measurement purposes.

Rather than using a specialized tool such as the tool 1200, a tool being using for performing a medical procedure such as the tool 600 may be used instead for performing the measurement described in reference to FIGS. 10 and 11 (as well as other measurement techniques described herein using the tool 1200). In this case, the tool 600 may be used in its closed position as shown in FIG. 14. Alternatively, it may be used in an open position with a reference point defined for measurement purposes at a mid-point position between tips E1, E2 or other calibrated point on the tool 600.

If the tool 600 is configured with a force sensor on the tip of either or both its first and second elements 601, 601, then contact of the force sensor with the left and right sides of the anatomic structure 520 may generate start and stop indications which the distance determination processor 402 may use to determine the width "w" of the anatomic structure 520 as described in reference to FIG. 10. On the other hand, if the tool 600 is not configured with a force sensor, then its contact with the left and right surfaces of the anatomic structure 520 may be determined from the master torque feedback command signals generated by a joint control unit in the master/slave control system which reflects forces being exerted against the tool 600, or such contact may be determined visually by the surgeon as he or she is viewing a captured image of the tool 600 and the anatomic structure 520 on the monitor 104. Either or both of the tools 1200-1, 1200-2 may be constructed as the tool 1200 or the tool 600.

After determining the distance moved by a tool as described in reference to FIGS. 6-14 above, the display processor 404 displays the distance information on the monitor 104 according to user selected display options provided through the graphical user interface 403. Examples of such display options are now described in reference to FIGS. 15-18 as follows. Although these examples use a single tool 1200, it is to be appreciated that two tools such as the tools 1200-1, 1200-2 may be used instead to concurrently (rather than sequentially) indicate points for distance measurements.

Figure 15:
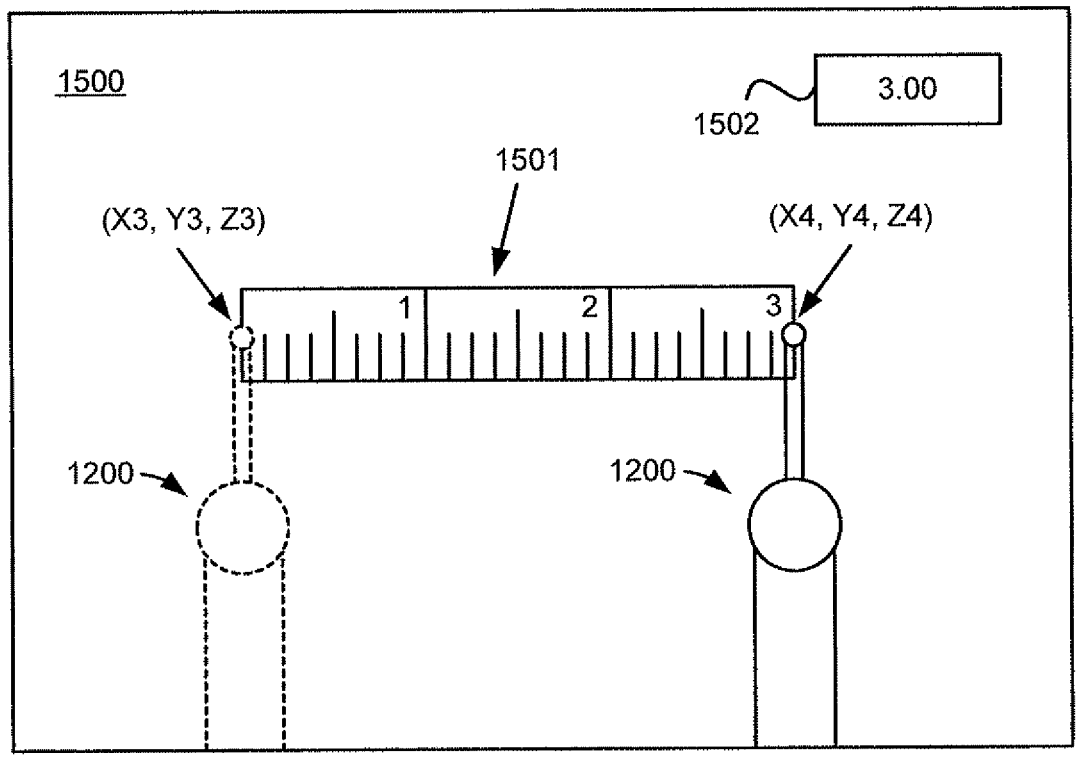
FIG. 15 illustrates a monitor screen displaying an image of a tool with information of a distance traversed by a tip of the tool used in a medical robotic system utilizing aspects of the present invention.

FIG. 15 illustrates, as an example, a display screen 1500 of the monitor 104, on which, an image of the tool 1200 and information of a distance traversed by the tip of the tool 1200 is shown. The image of the tool 1200 in this example was captured in vivo by an image capturing device such as the stereoscopic endoscope 140. Although the tool 1200 is shown in two-dimensions to simplify its illustration, it is to be appreciated that the monitor 104 displays three-dimensional images so that the surgeon viewing the monitor 104 actually sees a three-dimensional image of the tool 1200 as well as any other objects within the field-of-view of the image capturing device at the time.

As in previous examples, the tool 1200 is shown in dotted outline form to indicate a prior position of the tool 1200, and it is shown in solid outline form to indicate a current position of the tool 1200. The prior position in this case is when a start indication was issued by the surgeon to start determining distances traversed by the tip of the tool 1200 as it moves away from this position. Thus, for clarity, the prior position in this case is referred to as being the initial position. As the tool 1200 moves, a virtual or ghost image of the tool 1200 may optionally remain in the initial position on the display screen 1500 to provide a point of reference. The image of the virtual or ghost tool 1200 should be clearly different from that of the actual tool 1200 so as to distinguish it from the image of the actual tool 1200 on the display screen 1500.

The information of the distance traversed by the tip of the tool 1200 is shown in two ways on the display screen 1500. First, a virtual tape measure 1501 is shown which appears to be held by the tip of the ghost image of the tool 1200 at an initial position (X3, Y3, Z3) of the tip and to extend out to a current position (X4, Y4, Z4) of the tip as the image of the tool 1200 moves on the display screen 1500 in response to operator manipulation of its associated input device. Thus, the distance that the tip of the tool 1200 moves from its initial position may be read directly off the virtual tape measure 1501 at all times during its movement. In the present example, where the scale of the virtual tape measure 1501 is in inches and the displacement of the tool 1200 from its initial position is 3 inches, this distance is clearly shown on the extended end of the virtual tape measure 1501.

Although the virtual tape measure 1501 is shown as being held at its "0" end by the ghost image of the tool 1200 and its extended length read out at the image of the tool 1200 at its current position (X4, Y4, Z4), the computer generated image of the virtual tape measure 1501 may be reversed so that it appears to be held at its "0" end by the image of the tool 1200 at its current position (X4, Y4, Z4) and its extended length read out at the ghost image of the tool 1200. This reversed version of the virtual tape measure 1501 may provide better readability as the tool 1200 moves away from its initial position in three-dimensional space.

As a second way of displaying information of the distance traversed by the tip of the tool 1200 from its initial position (e.g., its position when a start indication was detected or otherwise received), a digital read-out 1502 is displayed on the display screen 1500 that is updated periodically to indicate the current distance of the tip of the tool 1200 from its initial position. The digital read-out 1502 may be provided in addition to the virtual tape measure 1501 or as an alternative to it. In the latter case, a line connecting the tips of the ghost image of the tool and the actual image of the tool 1200 may be drawn on the display screen 1500 so that the tip's movement from its initial position to its current position may be readily seen.

The digital read-out 1502 may also be used for displaying the displacement between the first and second elements of the measuring devices depicted and described in reference to FIGS. 6-9. In any application using the digital read-out 1502, the scale (e.g., inches, centimeters, millimeters, etc.) may be defined by operator selection using the graphical user interface unit 403.

Although the virtual tape measure is shown in FIG. 15 to have a linear scale measured in inches, alternatively it may have a metric scale measured in centimeters or millimeters, depending upon the typical distances to be measured. The scale may also have a non-linear portion, such as a logarithmic scale, to account for decreasing absolute accuracy as the distance measurement increases.

Figure 16:
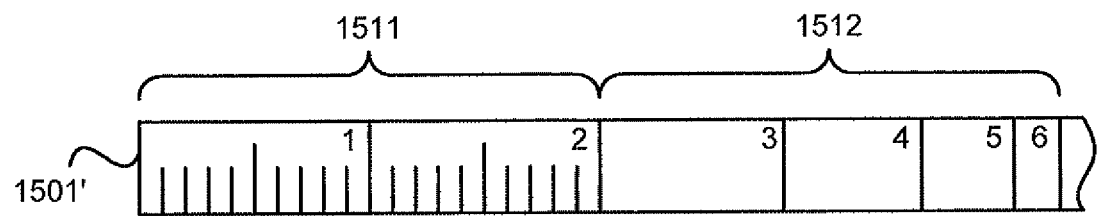
FIG. 16 illustrates a hybrid virtual tape measure having linear and non-linear scale parts as shown on a monitor for displaying information of a distance traversed by a tip of the tool used in a medical robotic system utilizing aspects of the present invention.

FIG. 16 illustrates, as an example, a hybrid virtual tape measure 1501' having a linear first part 1511 and a non-linear second part 1521, which may be provided as an alternative to the virtual tape measure 1501 shown in FIG. 15. The linear first part 1511 provides fine measurement of small distances and the non-linear second part 1521 provides coarse measurement of larger distances. The hybrid virtual tape measure 1501' is especially useful where it is being used to provide a quick sense of large tool distance movement to the surgeon, while a more precise measurement is provided through the digital read-out 1502. Of course, a completely non-linear virtual tape measure may also be provided in this latter case.

Figure 17:
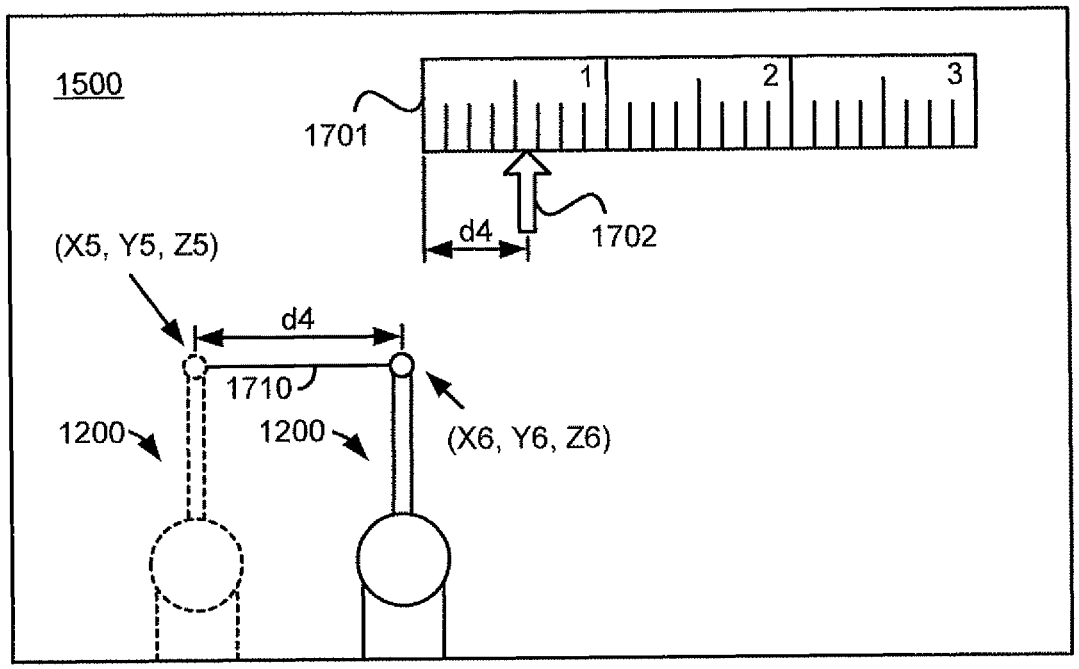
FIGS. 17-18 illustrate a virtual ruler with pointer useful for displaying information of a distance traversed by a tip of the tool used in a medical robotic system utilizing aspects of the present invention.
Figure 18:
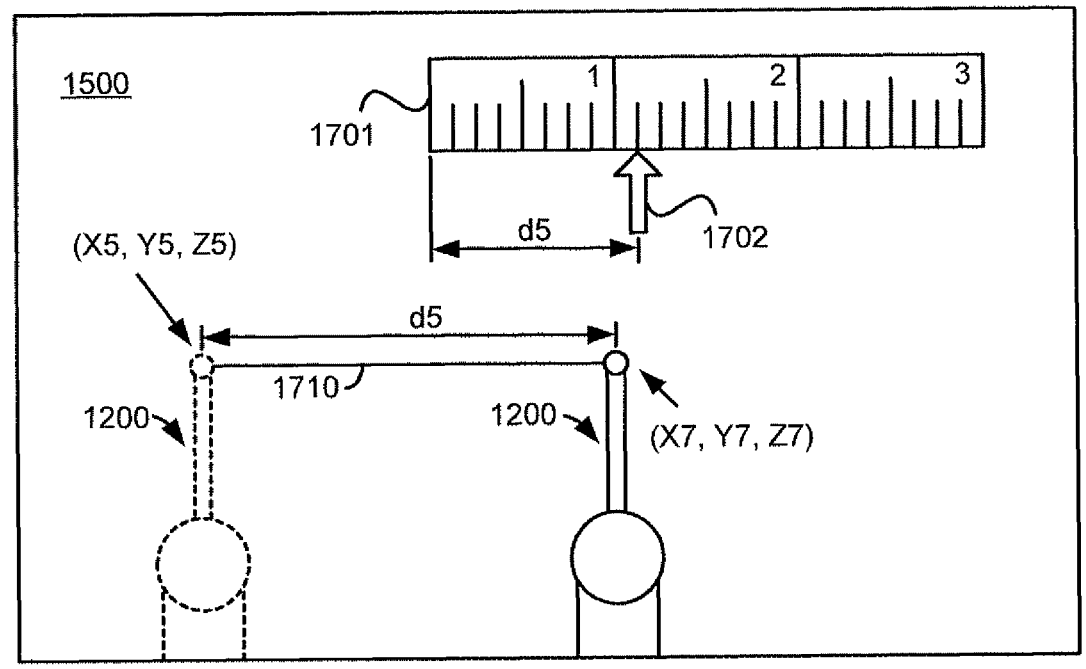

FIGS. 17-18 illustrate, as an example, another way of displaying information of the distance traversed by the tip of the tool 1200 from an initial position (X5, Y5, Z5) to a current position on the display screen 1500 of the monitor 104. In this example, the distance information is indicated using a virtual ruler 1701 and a pointer 1702 which are displayed on the display screen 1500. In both figures, the tool 1200 is shown in dotted outline form to indicate its initial position (X5, Y5, Z5), and shown in solid outline form to indicate its current position.

In FIG. 17, the current position of the tool's tip (at time "t1") is at point (X6, Y6, Z6) which results in a distance of "d4" from its initial position of (X5, Y5, Z5). To indicate this distance on the virtual ruler 1701, the pointer 1702 points to a point indicating the distance "d4" on the virtual ruler 1701. In FIG. 18, the current position of the tool's tip (at a subsequent time "t2") is at point (X7, Y7, Z7) which is a distance of "d5" from its initial position of (X5, Y5, Z5). To indicate this distance on the virtual ruler 1701, the pointer 1702 points to a point indicating the distance "d5" on the virtual ruler 1701. Thus, the pointer 1702 moves as the tool tip moves to visually associate the distance information indicated by the pointer 1702 with the movement of the tool 1200.

In FIGS. 17-18, it is worth noting that the scale factor between the distance shown between the initial and current positions of the tool tip and the distance indicated by the pointer 1702 on the virtual ruler 1701 is not necessarily one-to-one. For example, it is a two-to-one scale factor in the described embodiment. Other scale factors may also be used and are preferably selectable by the operator through the graphical user interface 403. It is also worth noting that although the virtual ruler 1701 is depicted as having a linear scale, it may also have a non-linear scale or hybrid scale such as the virtual tape measure 1501' depicted in FIG. 16.

To enhance visualization of the distance moved by the tool tip from its initial position, a straight line 1710 may be displayed on the display screen 1500 connecting the tool tips of the initial position ghost image of the tool 1200 and the captured image of the tool 1200 being displayed at the time on the display screen 1500.

Figure 19:
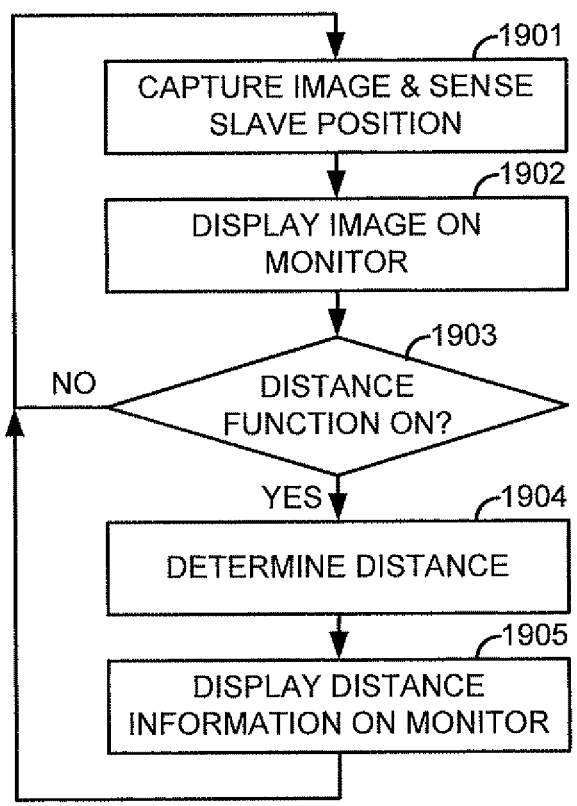
FIG. 19 illustrates a flow diagram of a method for determining and displaying information of an operator indicated distance using a medical robotic system utilizing aspects of the present invention.

FIG. 19 illustrates, as an example, a flow diagram of a method for determining and displaying information of an operator indicated distance using the medical robotic system 100.

In 1901, an image capturing device captures images of one or more tools being robotically manipulated by an operator of the medical robotic system 100, and encoders in slave manipulators manipulating the one or more tools sense the robotic manipulation of the one or more tools. In 1902, the captured images are processed and displayed on the monitor 104 of the medical robotic system 100.

In 1903, a determination is made whether a distance determination function is to be performed (i.e., whether the distance function is ON). As an example, the distance function may be ON only during a period which is initiated after receiving a start indication and ended after receiving a stop indication, wherein both the start and stop indications are initiated by the operator of the medical robotic system 100. Alternatively, the distance function may only be on for a short time after receiving a measurement command from an operator of the medical robotic system 100. As an example of this alternative case, the distance function may only be on for the period of time the system takes to detect the measurement command and perform the distance determination.

If the determination in 1903 is NO, then the method loops back to 1901 to continue to display periodically captured images of the one or more tools being robotically manipulated by the operator of the medical robotic system 100, and periodically sense the robotic manipulations of the one or more tools using the slave manipulator encoders.

On the other hand, if the determination in 1903 is YES, then the method proceeds to 1904 where an operator indicated distance is determined. In the case where only one tool is being used for such indication, the distance that the tool has moved relative to an initial position is determined. The initial position in this case is the position (e.g., Cartesian coordinate location in a fixed reference frame) that the tool was at when the start indication was received. The distance determination is performed using the sensed robotic manipulation of the tool. For example, the encoders in the slave manipulator may sense joint positions that are transformed into a current position of the tool using forward kinematics of the slave manipulator, and the distance may then be calculated using the current position of the tool relative to the initial position of the tool. The tool in this case may be the tool 1200 or the tool 600 or any other tool suitable for the performing the method, and the distance moved by the tool may relative to a reference point on the tool or a tip of the tool.

On the other hand, when two tools are used by the operator to indicate a distance to be determined (such as described in reference to FIG. 11), the distance between corresponding reference points on the two tools is determined. For example, a position relative to a fixed reference frame (such as the base of the patient-side cart 120) is determined for a reference point (such as the sensor 1202 of the tool 1200) on each of the two tools and the distance is then calculated between those two reference points using equation (3) as described above. The position determinations for the reference points may be performed from information provided by sensors in their respective slave manipulators or by other well known means.

In 1905, information of the determined distance is displayed on the monitor 104 along with the captured images of the one or more tools. Examples of such displaying of the distance information are provided and described in reference to FIGS. 15-18. The method then loops back to 1901 to continue to display captured images of the one or more tools being robotically manipulated by the operator of the medical robotic system 100 and continue to display the determined distance information according to 1903-1905.

Although the various aspects of the present invention have been described with respect to a preferred embodiment, it will be understood that the invention is entitled to full protection within the full scope of the appended claims.

We claim:

1. A method for determining and displaying information of an operator indicated distance using a medical robotic system, comprising:
   capturing images indicating movement of a tool as the tool is being robotically manipulated by a slave manipulator in response to operator manipulation of an input device;
   sensing joint positions of the slave manipulator;
   determining a distance moved by the tool using the sensed joint positions and forward kinematics of the slave manipulator; and
   displaying the captured images and information of the distance on a monitor of the medical robotic system so as to indicate movement of the tool and visually associate the information of the distance with the movement of the tool.

2. The method according to claim 1, further comprising: detecting an operator generated start indication, wherein the determination of the distance comprises determining the distance relative to an initial position of the tool at the time that the operator generated start indication is detected.

3. The method according to claim 2, wherein the displaying of the information of the distance on the monitor comprises: displaying a virtual tape measure on the monitor so that the virtual tape measure extends from the initial position of the tool to a current position of the tool so as to indicate the movement of the tool from the initial position of the tool.

4. The method according to claim 3, wherein the displaying of the information of the distance on the monitor comprises: displaying a digital read-out indicating an extension of the virtual tape measure on the monitor.

5. The method according to claim 1, wherein the movement of the tool comprises moving a first element of the tool relative to a second element of the tool, and the determination of the distance comprises determining a displacement of the first element relative to the second element.

6. The method according to claim 5, wherein proximal ends of the first and second elements are coupled together so that the displacement of the first element relative to the second element is determined by a separation between distal ends of the first and second elements.

7. The method according to claim 6, wherein the proximal ends of the first and second elements are coupled together at a pivot joint so that the first element moves relative to the second element by pivoting about the pivot joint.

8. The method according to claim 6, wherein the proximal ends of the first and second elements are coupled together so that the first element moves linearly relative to the second element by moving along a rail of the tool.

9. The method according to claim 1, wherein the displaying of the information of the distance on the monitor comprises: displaying a virtual ruler and a pointer on the monitor so that the pointer indicates the distance by pointing at a corresponding location on the virtual ruler.

10. The method according to claim 9, wherein the virtual ruler has a non-linear scale.

11. The method according to claim 9, wherein the virtual ruler has a first portion that has a linear scale and a second portion that has a non-linear scale.

12. The method according to claim 1, further comprising:
    periodically determining distances moved by the tool using the sensed robotic manipulation of the tool as the tool is being robotically manipulated by the operator; and
    displaying the information of the periodically determined distances on the monitor so as to visually associate the information with the movement of the tool.

13. A medical robotic system comprising:
    a tool;
    a robotic arm having a plurality of joints to move the tool and a plurality of sensors to sense movement of the plurality of joints;
    an image capturing device positioned to capture an image of the tool;
    a monitor;
    an input device; and
    a processor configured to move the robotic arm and the tool in response to operator manipulation of the input device, display images received from the image capturing device on the monitor, determine a distance moved by the tool using data received from the plurality of sensors and forward kinematics of the robotic arm, and display information of the determined distance on the monitor so as to indicate movement of the tool and visually associate the information of the distance with the movement of the tool.

14. The system according to claim 13, wherein the processor is configured to detect an operator generated start indication, and determine the distance the distance moved by the tool by determining the distance relative to an initial position of the tool at the time that the operator generated start indication is detected.

15. The system according to claim 14, wherein the processor is configured to display the information of the distance on the monitor by displaying a virtual tape measure on the monitor so that the virtual tape measure extends from the initial position to a current position of the tool so as to indicate the movement of the tool from the initial position of the tool.

16. The system according to claim 15, wherein the processor is configured to display the information of the distance on the monitor by displaying a digital read-out indicating an extension of the virtual tape measure on the monitor.

17. The system according to claim 13, wherein the movement of the tool comprises moving a first element of the tool relative to a second element of the tool, and the processor is configured to determine the distance moved by the tool by determining a displacement of the first element relative to the second element.

18. The system according to claim 17, wherein the processor is configured to determine the displacement of the first element relative to the second element by determining a separation between distal ends of the first and second elements.

19. The system according to claim 13, wherein the processor is configured to display the information of the distance on the monitor by displaying a virtual ruler and a pointer on the monitor so that the pointer indicates the distance by pointing at a corresponding location on the virtual ruler.

20. The system according to claim 19, wherein the virtual ruler has a first portion that has a linear scale and a second portion that has a non-linear scale.

21. A method for determining and displaying information of an operator indicated distance using a medical robotic system, comprising:

sensing joint positions of first and second slave manipulators respectively manipulating first and second tools;
   determining a distance between the first and second tools using the sensed joint positions and forward kinematics of the first and second slave manipulators; and
   displaying information of the distance on a monitor of the medical robotic system.

22. The method according to claim 21, wherein the displaying of the information of the distance on the monitor comprises: displaying a virtual tape measure on the monitor so as to extend between images of the first and second tools being displayed on the monitor.

23. The method according to claim 21, wherein the displaying of the information of the distance on the monitor comprises: displaying a digital read-out indicating the distance on the monitor.

24. The method according to claim 21, wherein the displaying of the information of the distance on the monitor comprises: displaying a virtual ruler and a pointer on the monitor so that the pointer indicates the distance by pointing at a corresponding location on the virtual ruler.

25. The method according to claim 24, wherein the virtual ruler has a non-linear scale.

26. The method according to claim 24, wherein the virtual ruler has a first portion that has a linear scale and a second portion that has a non-linear scale.

27. A medical robotic system comprising:
   a first tool;
   a first robotic arm having a first plurality of joints to move the first tool and a first plurality of sensors to sense movement of the first plurality of joints;
   a second tool;
   a second robotic arm having a second plurality of joints to move the second tool and a second plurality of sensors to sense movement of the second plurality of joints;
   a monitor;
   a first input device;
   a second input device; and
   a processor configured to move the first robotic arm and the first tool in response to operator manipulation of the first input device, move the second robotic arm and the second tool in response to operator manipulation of the second input device, determine a distance between the first and second tools using data received from the first and second pluralities of sensors and forward kinematics of the first and second robotic arms, and display information of the determined distance on the monitor.

28. The system according to claim 27, wherein the processor is configured to display the information of the distance on the monitor by displaying a virtual tape measure on the monitor so as to extend between images of the first and second tools being displayed on the monitor.

29. The system according to claim 27, wherein the processor is configured to display the information of the distance on the monitor by displaying a digital read-out indicating the distance on the monitor.

30. The system according to claim 27, wherein the processor is configured to display the information of the distance on the monitor by displaying a virtual ruler and a pointer on the monitor so that the pointer indicates the distance by pointing at a corresponding location on the virtual ruler.

31. The system according to claim 30, wherein the virtual ruler has a first portion that has a linear scale and a second portion that has a non-linear scale.

* * * * *